US00PP29009P2

(12) United States Plant Patent
Lommerse

(10) Patent No.: US PP29,009 P2
(45) Date of Patent: Feb. 27, 2018

(54) ***STEVIA* PLANT NAMED 'STEVILOMM'**

(50) Latin Name: ***Stevia rebaudiana* (Bertoni) Bertoni**
Varietal Denomination: STEVILOMM

(71) Applicant: Lommerse Holding BV, Mariahout (NL)

(72) Inventor: Henry C. Lommerse, Mariahout (NL)

(73) Assignee: Lommerse Holding BV, Mariahout (NL)

( * ) Notice: Subject to any disclaimer, the term of this patent is extended or adjusted under 35 U.S.C. 154(b) by 0 days.

(21) Appl. No.: 15/530,310

(22) Filed: Dec. 22, 2016

(51) Int. Cl.
*A01H 5/02* (2006.01)

(52) U.S. Cl.
USPC ..... Plt./258

(58) Field of Classification Search
USPC ..... Plt./258, 263.1
See application file for complete search history.

*Primary Examiner* — Annette H Para
(74) *Attorney, Agent, or Firm* — Samuel R. McCoy Jr.

(57) ABSTRACT

A new and distinct *Stevia* cultivar named 'STEVILOMM' which is characterized by the combination of vigorous growth, high tolerance to adverse growing conditions, a high concentration sweetening compounds in the foliage, a large amount of harvestable dry foliage, and the stability of these characteristics from generation to generation.

3 Drawing Sheets

Latin name of the genus and species: The Latin name of the genus and species of the novel variety disclosed herein is *Stevia rebaudiana* (Bertoni) Bertoni.

Variety denomination: The inventive cultivar of *Stevia* disclosed herein has been given the variety denomination 'STEVILOMM'.

BACKGROUND OF THE INVENTION

Parentage: The *Stevia* cultivar 'STEVILOMM' is the result of a planned breeding program carried out by the inventor at his greenhouse in Mariahout, the Netherlands. In May of 2013, the inventor performed a controlled cross-pollination of the seed parent, *Stevia* '3660/12' (not patented), with *Stevia* '3666/12' (not patented), the pollen parent. In March of 2014, a seedling that exhibited potential commercial value was selected from all other progeny. The seedling was given the reference code "5992/14" and allowed to grow to a mature size, for further evaluation. In the summer of 2014, the candidate was asexually propagated using softwood cuttings to assess the stability of the unique characteristics for which the candidate was originally selected. In April of 2015, a final selection was made and the new cultivar was given the name 'STEVILOMM'.

Asexual Reproduction: Asexual reproduction of 'STEVILOMM', by way of softwood stem cuttings, was first performed in the summer of 2014 at the inventor's greenhouse in Mariahout, the Netherlands and has since been further cloned using meristematic tissue culture propagation. Through three subsequent generations, the unique features of this cultivar have proven to be stable and true to type.

SUMMARY OF THE INVENTION

The cultivar 'STEVILOMM' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'STEVILOMM'. These characteristics in combination distinguish 'STEVILOMM' as a new and distinct *Stevia* cultivar:

1. *Stevia* 'STEVILOMM' exhibits foliage with high levels of steviosides and rebaudioside A, and low levels of rebaudioside C resulting in a high concentration of sweetening compounds; and
2. *Stevia* 'STEVILOMM' exhibits vigorous growth and free branching which results in a large amount of harvestable dry foliage; and
3. *Stevia* 'STEVILOMM' exhibits improved tolerance to heat, cold, and heavy rain which results in a large amount of harvestable dry foliage under adverse growing conditions.

BOTANICAL DESCRIPTION OF THE PLANT

Figure 1:
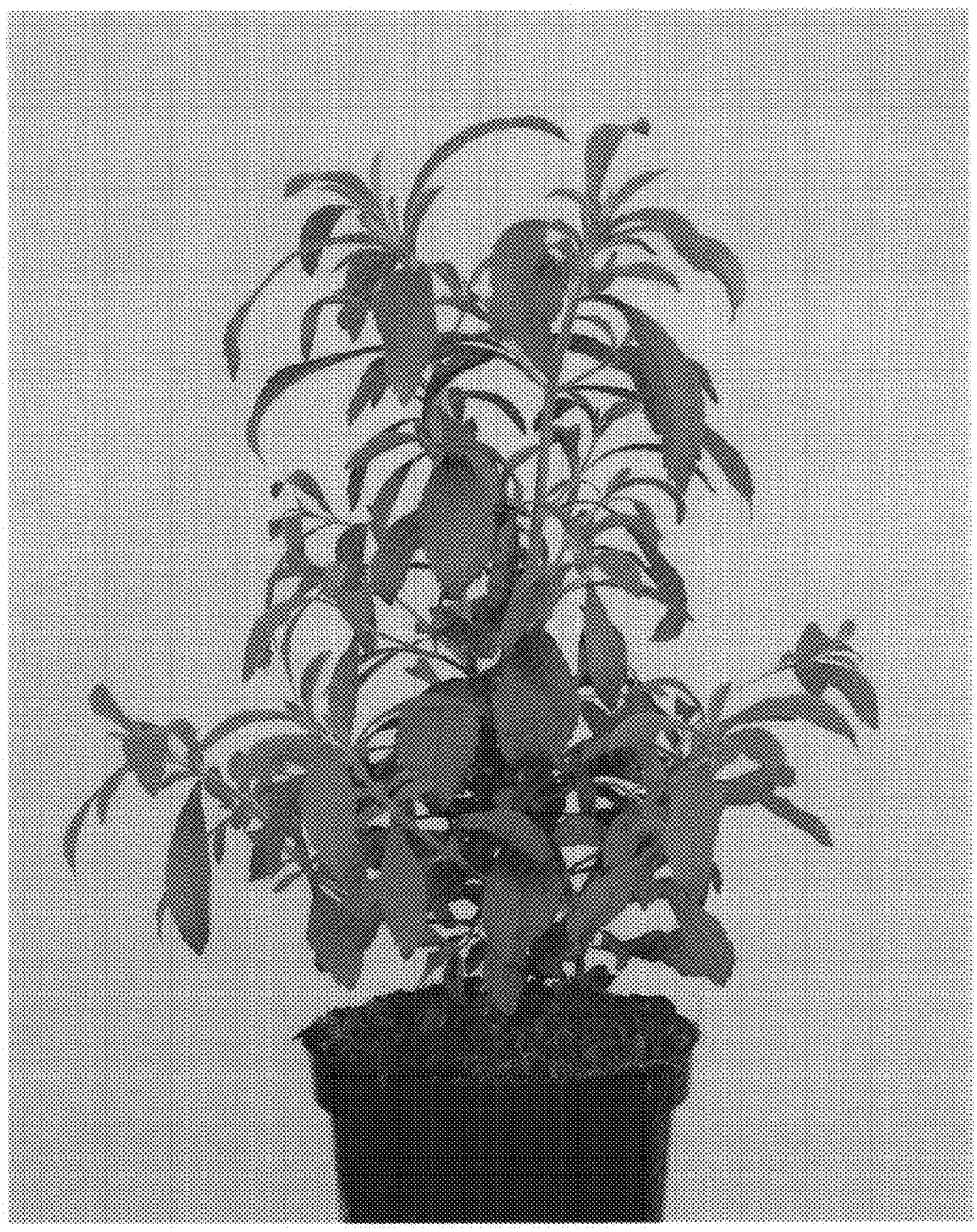
FIG. 1 illustrates, as nearly true as it is reasonably possible to make the same in color photographs of this type, an exemplary plant of 'STEVILOMM' grown in a greenhouse in Mariahout, the Netherlands. This plant, grown in a 17 cm nursery container, is approximately 8 weeks old from a rooted young plant.
Figure 2:
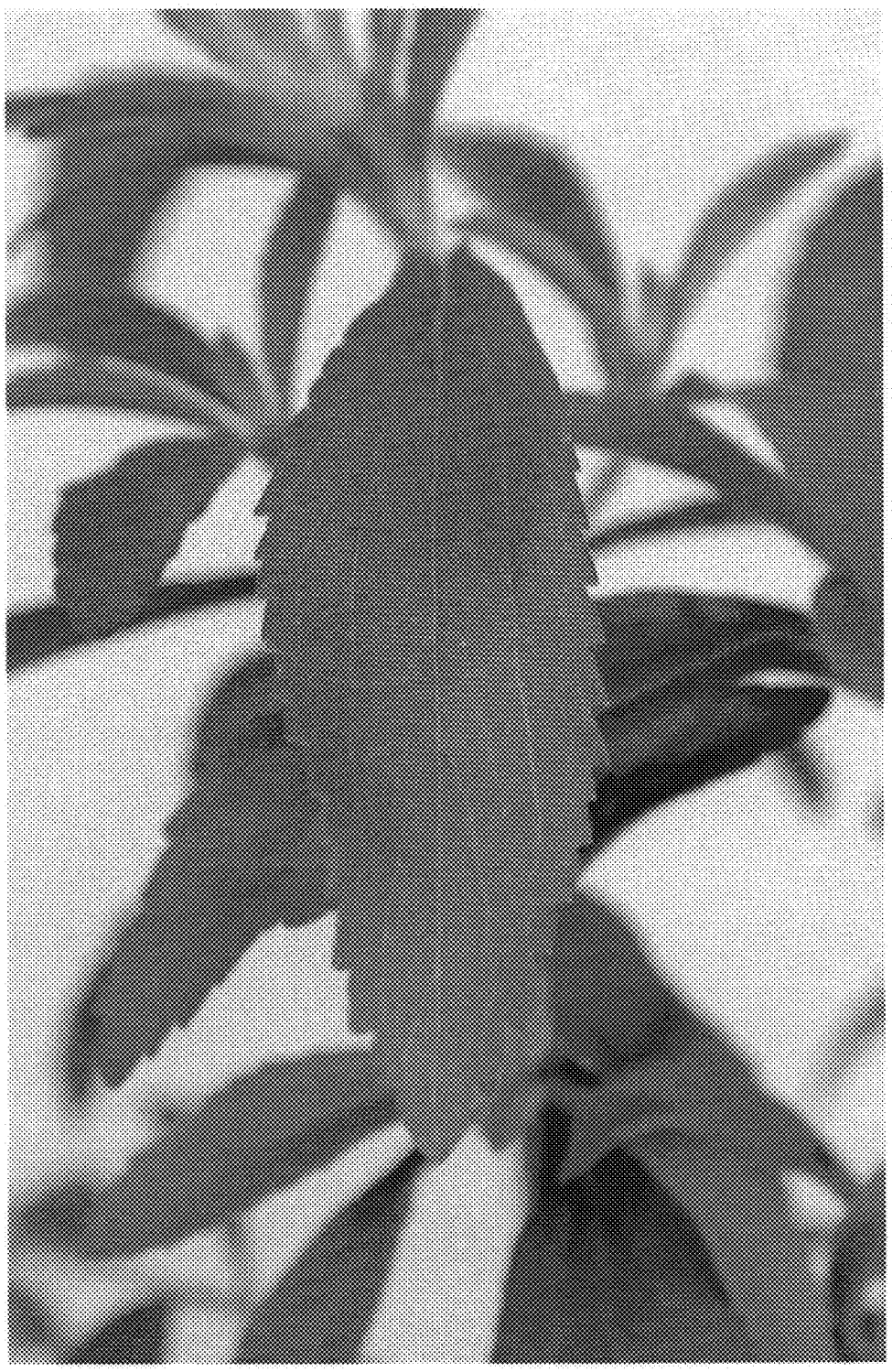
FIG. 2 illustrates, as nearly true as it is reasonably possible to make the same in color photographs of this type, the typical foliage of 'STEVILOMM'.
Figure 3:
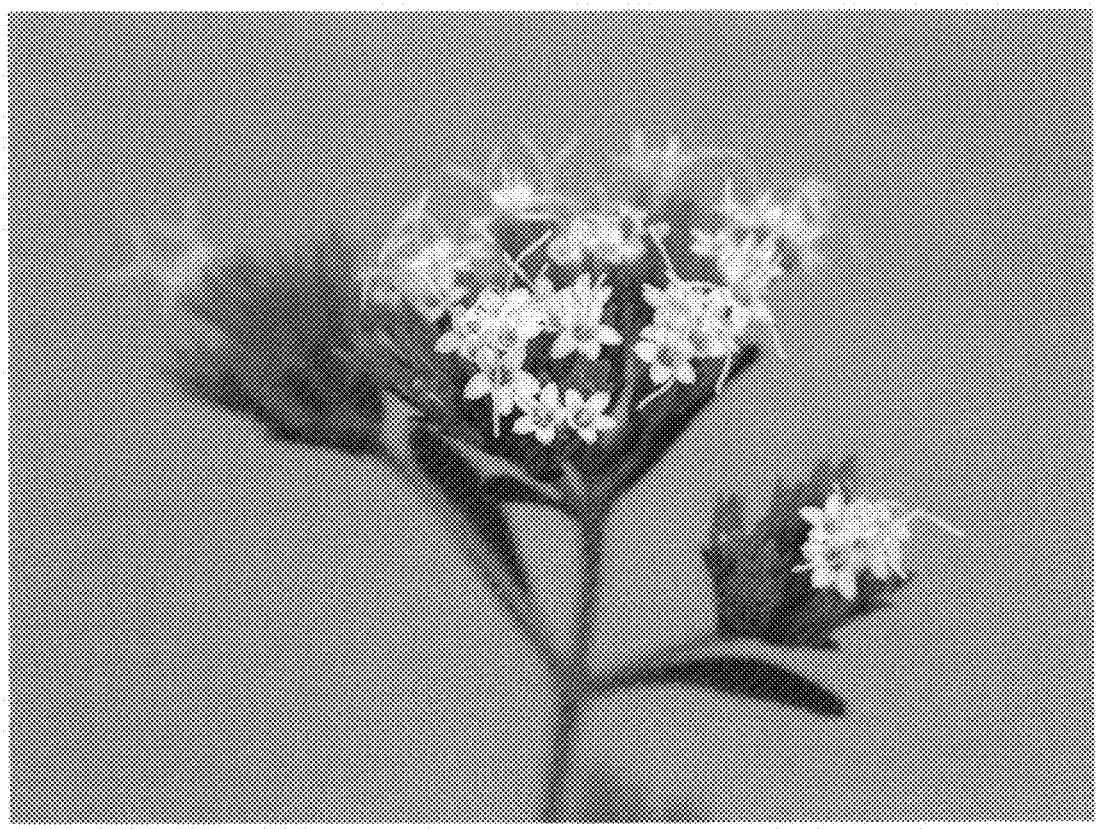
FIG. 3 illustrates, as nearly true as it is reasonably possible to make the same in color photographs of this type, the typical inflorescence and flowers of 'STEVILOMM'.

With the exception of the inflorescence and flower descriptions, the following observations and measurements made in June of 2016 describe averages from a sample set of six specimens of 8 week old 'STEVILOMM' plants grown in 17 cm nursery pots in a greenhouse in Mariahout, the Netherlands. The inflorescence and flower descriptions were made in October of 2016 from 24 week old 'STEVILOMM' plants grown in 17 cm nursery pots in a greenhouse in Mariahout, the Netherlands. Plants were produced without supplemental light, under shade cloth, using drip irrigation at regular intervals, and fertilized as required using a fertilizer with an analysis of 18-18-18-5. No chemical treatments of any kind were utilized.

Those skilled in the art will appreciate that certain characteristics will vary with older or, conversely, with younger plants. 'STEVILOMM' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'STEVILOMM' and comparisons with the parent plants and most similar commercial *Stevia* cultivar known to the inventor are provided below.

Plant description:

*Growth habit*.—Perennial; broad upright.

*Plant shape*.—Ovate.

*Average height from base to top of foliage*.—40.5 cm.

*Average height from base to top of the floral plane*.—58.3 cm.

*Average width*.—Average of 35.2 cm.

*Growth rate*.—Moderate.

*Plant vigor*.—Moderate.

*Propagation details*.—Asexual propagation is accomplished by both softwood stem cuttings and also by mericloning.

*Time to initiate roots*.—After deflasking the micropropagule, approximately 15 days are required for the propagule to initiate roots at 20 degrees Celsius.

*Time to produce a marketable* 17 *cm potted plant*.—Approximately 12 weeks.

*Disease and pest resistance or susceptibility*.—Similar to other *Stevia rebaudiana* varieties.

*Environmental tolerances*.—Adapt to at least USDA Zones 11 and 12 and temperatures as high as 40 degrees Celsius; moderate tolerance to rain; low tolerance to wind.

Root system:

*General*.—Moderately dense rooting.

*Dimensions, mature roots*.—24.0 cm long with a diameter of 0.1 cm, on average.

*Texture*.—Non-fleshy; slightly fibrous.

*Color*.—White, RHS 155A; older roots are greyed-orange, in between RHS N170B and N170C.

Stems:

*Branching habit*.—Main stems grow from the base, freely branching with lateral branches.

*Number of main stems per plant*.—2.

*Number of lateral branches per plant*.—23.

*Appearance and shape*.—Rounded.

*Length of lateral branches*.—11.5 cm.

*Diameter of lateral branches*.—Averaging 0.3 cm at the widest point.

*Internode length on lateral branches*.—4.2 cm.

*Luster*.—Moderately glossy.

*Aspect*.—Average angle is approximately 60 degrees from vertical.

*Strength*.—Strong.

*Color, juvenile*.—Yellow-green, RHS 144B.

*Color, mature*.—Yellow-green, a mixture of RHS 144B and 145A.

*Color at internodes*.—Yellow-green, a mixture of RHS 144B and 145A.

*Color of oldest wood*.—Yellow-green, RHS 146D.

*Pubescence*.—Stems are densely covered with a soft pubescence; average length of hairs is 0.1 cm; hairs are colored white to green-white, a mixture of RHS NN155B and 157D.

Foliage:

*General description*.—Foliage is edible with a very sweet taste due to the high concentration of steviosides.

*Arrangement*.—Opposite.

*Division*.—Simple.

*Number of leaves per lateral branch*.—6.

*Lamina*.—Dimensions — 9.7 cm long and 3.1 cm wide, on average. Shape — Oblanceolate. Aspect — Slightly curved downwards. Apex — Bluntly acute. Base — Long attenuate. Margin — Serrate. Pubescence, adaxial surface — Moderately to densely covered with very short appressed hairs of approximately 0.4 mm; hairs colored white to green-white, RHS NN155B to 157D. Texture and luster of adaxial surface — Smooth and very slightly glossy. Pubescence, abaxial surface — Moderately to densely covered with very short hairs of approximately 0.4 mm; hairs colored white to green-white, a mixture of RHS NN155B and 157D. Texture and luster of abaxial surface — Slightly rugose and matte. Color — Juvenile foliage, adaxial surface — Green, in between RHS 143A to 143B. Juvenile foliage, abaxial surface — A mixture of green, RHS 143C, and yellow-green, RHS 144A. Mature foliage, adaxial surface — Green, RHS 137B. Mature foliage, abaxial surface — Yellow-green, a mixture of RHS 146B and 147B. Venation — Pattern — Pinnate. Color, adaxial surface — Yellow-green, RHS 146C. Color, abaxial surface — Yellow-green, in between RHS 144B and 144C.

*Sheath*.—Not sheathing.

*Petiole*.—Length — Average of 0.6 cm. Width — Petioles are flattened; average horizontal width is 0.2 cm and the average vertical width is 0.125 cm. Texture — Pubescent. Luster — Moderately glossy. Strength — Moderately strong. Color, adaxial surface — Yellow-green, RHS 144C. Color, abaxial surface — Yellow-green, RHS 144B.

*Dry weight of glycosides to dry weight of leaf material*.—Stevioside — 9.4%. Rebaudioside A — 2.5%. Rebaudioside C — 0.7%. Dulcoside A — 0.4%.

Inflorescence:

*Inflorescence arrangement*.—Terminal capitula in a compound cyme.

*Natural flowering season*.—Autumn.

*Time to flower*.—10 months.

*Quantity of flowers per inflorescence*.—20 capitula.

*Quantity of flowers per plant*.—50 capitula.

*Quantity of flower buds per plant*.—450 capitula.

*Quantity of flowers and flower buds per plant*.—500 capitula.

*Inflorescence height*.—3.2 cm.

*Inflorescence diameter*.—3.8 cm.

*Terminal peduncle*.—Length — 0.9 cm. Diameter — 0.08 cm. Strength — Moderately strong. Texture —

Densely covered with a soft pubescence; hairs with an average length of 0.1 cm; color of hairs is a mixture of white to green-white, nearest to RHS NN155B and RHS 157D. Luster — Matte. Color — Yellow-green, RHS 145A.

*Axillary peduncle*.—Length — 1.1 cm. Diameter — 0.08 cm. Attitude; angle to the stem — 45 degrees from the stem. Strength — Moderately strong. Texture — Densely covered with a soft pubescence; hairs with an average length of 0.1 cm; color of hairs is a mixture of white to green-white, nearest to RHS NN155B and RHS 157D. Luster — Matte. Color — Yellow-green, RHS 145A.

Flower buds:

*Shape*.—Oblanceolate.

*Height*.—0.7 cm.

*Diameter*.—0.3 cm.

*Texture*.—Moderately pubescent with very short hairs, colored yellow-green, nearest to RHS 145C.

*Luster*.—Matte.

*Color*.—Yellow-green, nearest to RHS 144B.

Flower:

*Flower type*.—Composite; capitula.

*Flowering habit*.—Freely flowering.

*Aspect*.—Upright to slightly outward.

*Fragrance*.—None.

*Flower longevity*.—One week, on average.

*Persistence*.—Persistent.

*Disc diameter*.—0.9 cm.

*Receptacle shape*.—Inverted triangular.

*Receptacle height*.—0.05 cm.

*Receptacle diameter*.—0.05 cm.

*Receptacle color*.—Yellow-green, nearest to RHS 144A.

*Ray florets*.—None present.

*Disc florets*.—Quantity of florets per capitula — Five. Shape — Tubular. Arrangement — Radial symmetry; one whorl; florets are unfused. Attitude — Upright. Length — 1.0 cm. Diameter, including stigmas — 0.5 cm, on average. Diameter, excluding stigmas — 0.3 cm, on average. Color, upper and lower surfaces — White, in between RHS 155C and 155D. Apex — Acute. Base — Fused into a tube. Margin — Entire; not undulated. Texture and luster, upper surface — Smooth, velvety and matte. Texture and luster, lower surface — Smooth, velvety and matte. Color, when opening, upper surface — White, nearest to NN155C; throat is yellow-green, nearest to RHS 150D; tube is colored slightly darker, nearest to RHS 145D. Color, when opening, lower surface — White, nearest to NN155C; throat is yellow-green, nearest to RHS 150D; tube is colored slightly darker, nearest to RHS 145D. Color, when fully opened, upper surface — White, nearest to NN155C; throat is yellow-green, nearest to RHS 150D; tube is colored slightly darker, nearest to RHS 145D. Color, when fully opened, lower surface — White, nearest to NN155C; throat is yellow-green, nearest to RHS 150D; tube is colored slightly darker, nearest to RHS 145D. Venation, when fully opened, upper surface — White, nearest to NN155C; throat is yellow-green, nearest to RHS 150D; tube is colored slightly darker, nearest to RHS 145D. Venation, when fully opened, lower surface — White, nearest to NN155C; throat is yellow-green, nearest to RHS 150D; tube is colored slightly darker, nearest to RHS 145D.

*Involucre; phyllaries*.—Arrangement — Rotate; one whorl around the disc. Quantity — Five. Length — 0.7 cm. Width — 0.125 cm. Shape — Narrow oblong. Apex — Acute. Base — Cuneate. Margin — Entire. Texture, upper surface — Sparsely to moderately pubescent; average length of hairs is 0.05 cm; color is green-white, nearest to RHS 157D. Texture, lower surface — Sparsely to moderately pubescent; average length of hairs is 0.05 cm; color is green-white, nearest to RHS 157D. Luster, upper surface — Matte. Luster, lower surface — Matte. Color, upper surface — In between green, nearest to RHS 143B, and yellow-green, nearest to RHS 144A. Color, lower surface — In between green, nearest to RHS 143B, and yellow-green, nearest to RHS 144A.

*Pedicels*.—Length — 0.2 cm. Diameter — 0.08 cm. Attitude; angle to the peduncle — 15 degrees. Strength — Moderately strong. Texture — Densely covered with a soft pubescence; hairs with an average length of 0.1 cm; color of hairs is a mixture of white to green-white, nearest to RHS NN155B and RHS 157D. Luster — Matte. Color — Yellow-green, RHS 145A.

Reproductive organs:

*Androecium*.—Stamen quantity — 5. Filament length — 0.2 cm. Filament color — Yellow-green, nearest to RHS 145C. Anther shape — Linear. Anther length — 0.15 cm. Anther width — 0.03 cm. Anther color — Yellow-green, nearest to RHS 153D. Pollen, presence — Low. Pollen color — Yellow, nearest to 11D.

*Gynoecium*.—Pistil quantity — One. Pistil length — 0.7 cm. Style length — 0.6 cm. Style color — Green-white, nearest to RHS 157C. Stigma shape — Cleft, decurrent. Stigma length — 0.1 cm. Stigma diameter — 0.6 cm. Stigma color — White, nearest to RHS NN155C. Ovary color — Yellow-green, RHS 144C.

Seed and fruit: Not observed.

COMPARISONS WITH THE PARENT PLANT

Plants of the new cultivar 'STEVILOMM' may be distinguished from its seed parent, *Stevia* '3660/12', by the characteristics described in Chart 1.

CHART 1

| Characteristic | 'STEVILOMM' | '3660/12' |
|---|---|---|
| Plant habit. | Broad upright. | Upright. |
| Percent of rebaudioside A to total steviol glycoside content. | 17.8 percent. | 22.7 percent. |
| Percent of stevioside to total steviol glycoside content. | 66.3 percent. | 65.7 percent. |
| Percent of rebaudioside C to total steviol glycoside content. | 5.0 percent. | 5.7 percent. |

Plants of the new cultivar 'STEVILOMM' may be distinguished from its pollen parent, *Stevia* '3666/12', by the characteristics described in Chart 2.

CHART 2

| Characteristic | 'STEVILOMM' | '3666/12' |
|---|---|---|
| Plant habit. | Broad upright. | Broad. |
| Percent of rebaudioside A to total steviol glycoside content. | 17.8 percent. | 24.4 percent. |
| Percent of stevioside to total steviol glycoside content. | 66.3 percent. | 63.7 percent. |
| Percent of rebaudioside C to total steviol glycoside content. | 5.0 percent. | 5.4 percent. |

COMPARISON WITH THE MOST SIMILAR *STEVIA* CULTIVAR KNOWN TO THE INVENTOR

Plants of the new cultivar 'STEVILOMM' are most similar to the commercial variety, *Stevia rebaudiana* 'Sugarlove' (not protected in the United States). A comparison of 'STEVILOMM' with 'Sugarlove' is described in Chart 3.

CHART 3

| Characteristic | 'STEVILOMM' | 'Sugarlove' |
|---|---|---|
| Plant height. | 40.5 cm. | 49.8 cm. |
| Quantity of lateral branches. | 23, on average. | 9, on average. |
| Length of lateral branches. | 11.5 cm. | 31.3 cm. |
| Internode length. | 4.2 cm. | 5.7 cm. |
| Leaf dimensions. | 9.7 cm long and 3.1 cm wide. | 6.3 cm long and 2.5 cm wide. |

That which is claimed is:

1. A new and distinct cultivar of *Stevia* plant named 'STEVILOMM', substantially as described and illustrated herein.

* * * * *